US006804381B2

(12) United States Patent
Pang et al.

(10) Patent No.: US 6,804,381 B2
(45) Date of Patent: Oct. 12, 2004

(54) METHOD OF AND DEVICE FOR INSPECTING IMAGES TO DETECT DEFECTS

(75) Inventors: Kwok-Hung Grantham Pang, Pokfulam (HK); Ajay Kumar, Pokfulam (HK)

(73) Assignee: The University of Hong Kong, Hong Kong (CN)

(*) Notice: Subject to any disclaimer, the term of this patent is extended or adjusted under 35 U.S.C. 154(b) by 0 days.

(21) Appl. No.: 09/837,065

(22) Filed: Apr. 18, 2001

(65) Prior Publication Data

US 2002/0054293 A1 May 9, 2002

Related U.S. Application Data

(60) Provisional application No. 60/197,708, filed on Apr. 18, 2000.

(51) Int. Cl.[7] .................................................. G06K 9/00
(52) U.S. Cl. ........................ 382/111; 382/260; 356/430; 356/238.2
(58) Field of Search ................................. 382/111, 141, 382/173, 260, 264, 270; 348/88, 92, 125, 128; 356/430, 431, 238.1, 238.2, 238.3; 162/198

(56) References Cited

U.S. PATENT DOCUMENTS

| 4,124,300 A |   | 11/1978 | Mead et al. ................. 356/429 |
| 4,630,304 A |   | 12/1986 | Borth et al. ................... 381/94 |
| 4,975,971 A | * | 12/1990 | Ohnishi .......................... 382/8 |
| 5,301,129 A |   | 4/1994  | McKaughan et al. ....... 364/552 |
| 5,315,367 A | * | 5/1994  | Salvador et al. ............ 356/238 |
| 5,665,907 A |   | 9/1997  | Sheen et al. ................... 73/159 |
| 5,737,072 A |   | 4/1998  | Emery et al. ................. 356/73 |
| 5,740,048 A |   | 4/1998  | Abel et al. .................. 364/443 |
| 5,774,177 A |   | 6/1998  | Lane ........................... 348/88 |
| 5,815,198 A |   | 9/1998  | Vachtsevanos et al. ....... 348/88 |
| 5,825,501 A |   | 10/1998 | Mee et al. ................... 356/429 |
| 6,023,334 A |   | 2/2000  | Itagaki et al. ............... 356/376 |
| 2002/0110269 A1 | * | 8/2002 | Floeder et al. .............. 382/141 |

FOREIGN PATENT DOCUMENTS

| EP | 0 742 431 A1 | 11/1996 | .......... G01N/21/89 |
| EP | 0 974 831 A2 | 1/2000  | .......... G01N/21/89 |

* cited by examiner

Primary Examiner—Andrew W. Johns
(74) Attorney, Agent, or Firm—Dickstein, Shapiro, Morin & Oshinsky, LLP.

(57) ABSTRACT

The present invention relates to a method for automated defect detection in textured materials. The present invention utilizes linear Finite Impulse Response (FIR) filters with optimized energy separation. Specifically, the invention provides a method of inspecting industrial products for defects. The method has steps of: automated design of optimized filters from samples of products, using these optimal filters to filter the acquired images of product under inspection, computing the energy of each pixel in a local region, and finally segmenting the defect by thresholding each pixel. The present invention also relates to a method of inspection of unknown (unsupervised) defects in web materials. In an unsupervised inspection, information from a finite number of optimal filters is combined using a data fusion module. This module attempts to nullify the false alarm associated with the information arriving from different channels.

18 Claims, 17 Drawing Sheets

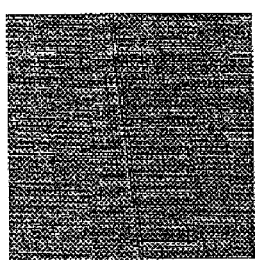 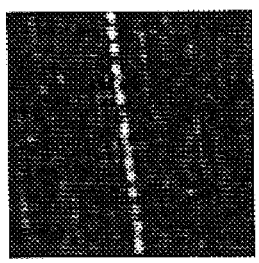 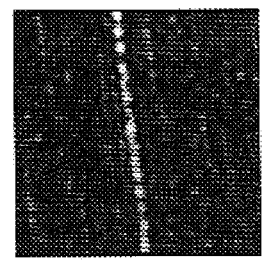 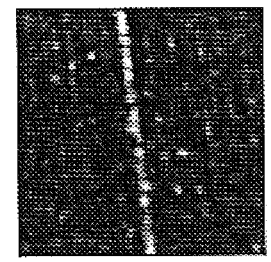
FIG.4(a)   FIG.4(b)   FIG.4(c)   FIG.4(d)
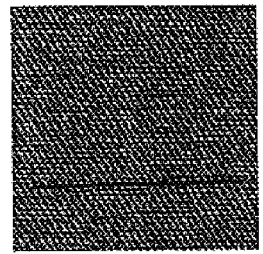 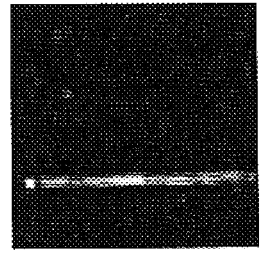 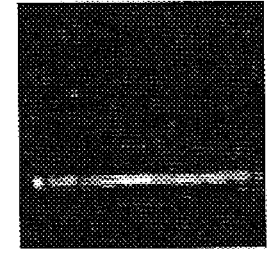 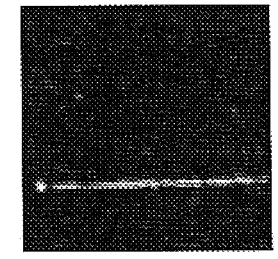
FIG.4(e)   FIG.4(f)   FIG.4(g)   FIG.4(h)

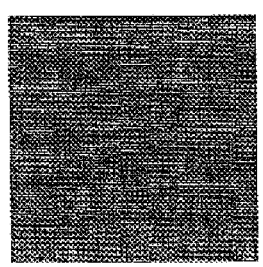 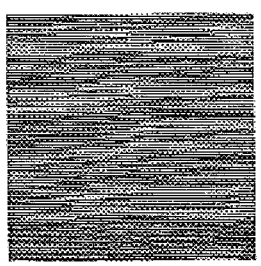 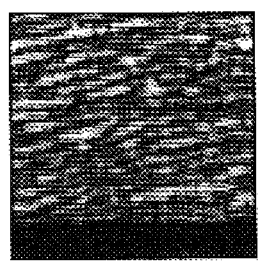 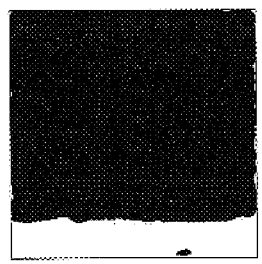
FIG.5(a)   FIG.5(b)   FIG.5(c)   FIG.5(d)
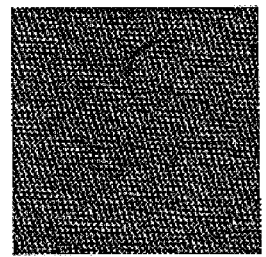 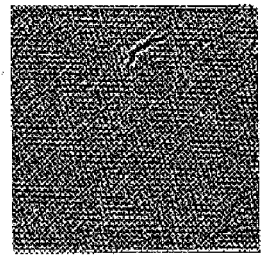 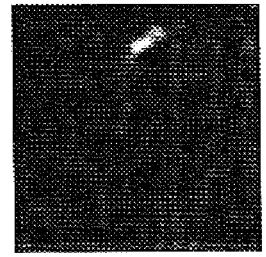 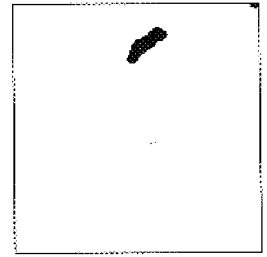
FIG.5(e)   FIG.5(f)   FIG.5(g)   FIG.5(h)

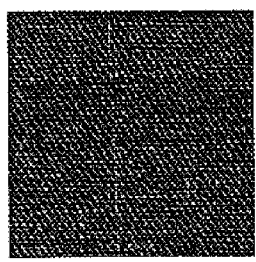 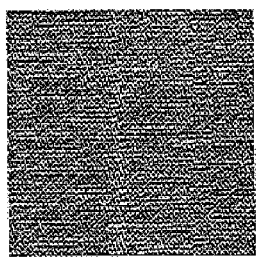 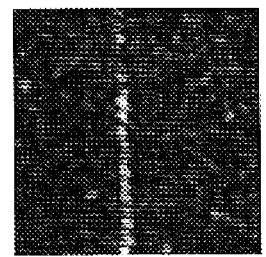 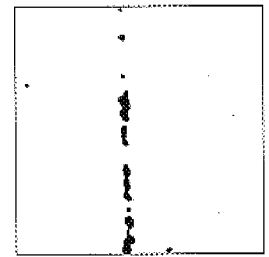
FIG.5(i)     FIG.5(j)     FIG.5(k)     FIG.5(l)
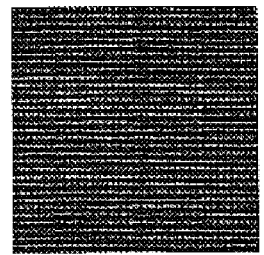 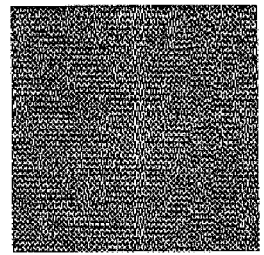 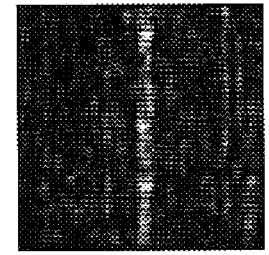 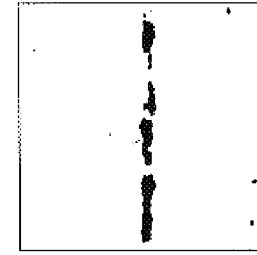
FIG.5(m)     FIG.5(n)     FIG.5(o)     FIG.5(p)

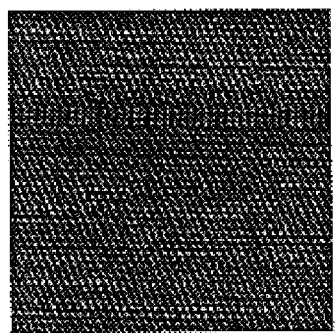 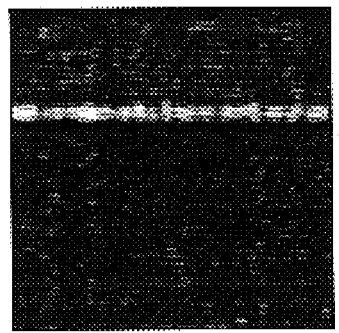 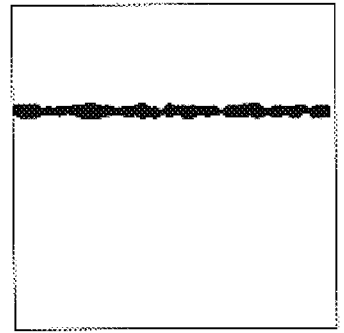
FIG.6(a)  FIG.6(b)  FIG.6(c)
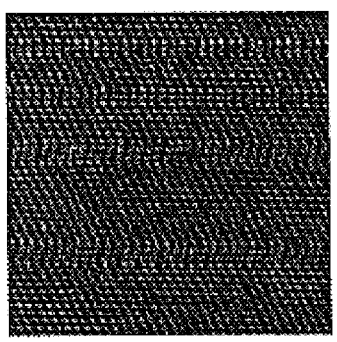 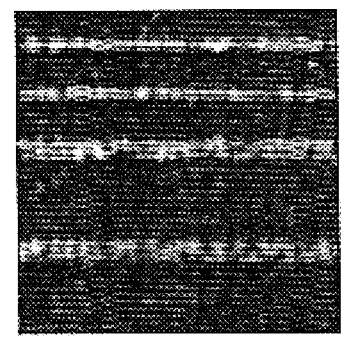 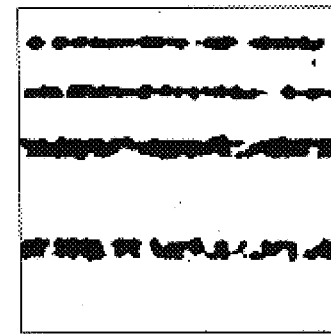
FIG.6(d)  FIG.6(e)  FIG.6(f)

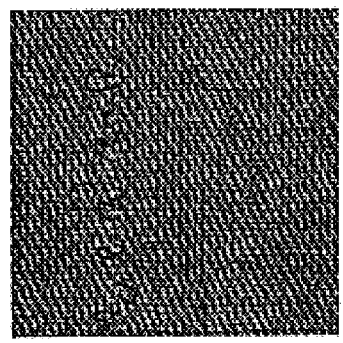 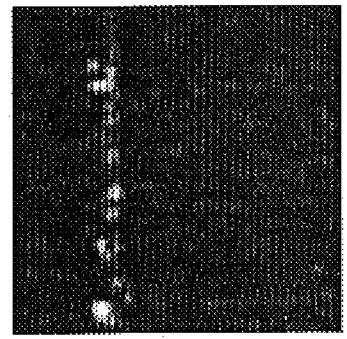
FIG.14(a)　　　FIG.14(b)
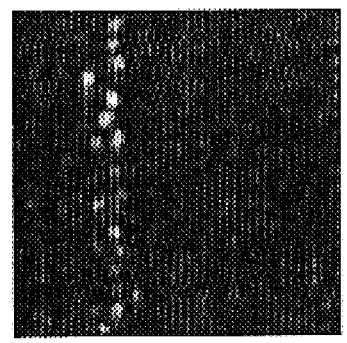 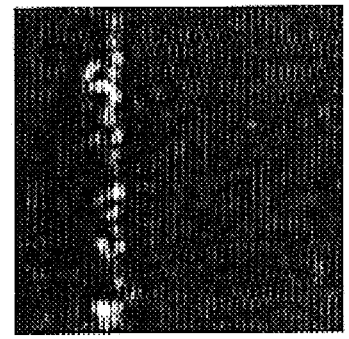
FIG.14(c)　　　FIG.14(d)
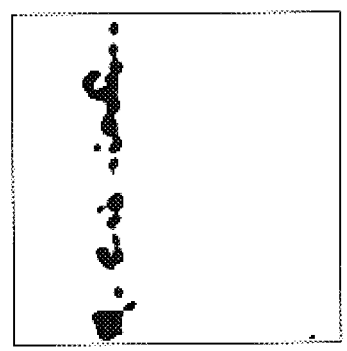
FIG.14(e)

METHOD OF AND DEVICE FOR INSPECTING IMAGES TO DETECT DEFECTS

This Application claims the benefit of Provisional Application No. 60/197,708 filed Apr. 18, 2000.

FIELD OF THE INVENTION

The present invention relates generally to a method of and device for inspecting images to detect defects. In particular, the present invention relates to a method and device for inspecting textured materials to detect defects therein.

DESCRIPTION OF THE PRIOR ART

Automated manufacture requires automated inspection of industrial materials, such as textile, paper, and plastic. Automated inspection of industrial materials needs adaptive solutions that can be executed in real time. Currently, a key element of quality assurance in production lines is manual inspection. Manual inspection is labor intensive and insufficient to maintain quality standards at high-speed production. For example in textile industry only about 70% of defects are being detected by manual inspection even with highly trained inspectors. Therefore automation of visual inspection task is desired to increase the efficiency of production lines and to improve quality of product as well.

Industrial inspection has extremely high requirements and is most challenging as compared to other inspection problems. A typical web is 6–10 feet wide and is processed at the speed of 20–60 m/min. Consequently the throughput for 100% inspection is tremendous, e.g., 10–15 MB image data per second when using line-scan camera. Therefore most feasible solutions require additional hardware components and reduction in calculation complexity.

Defect detection in industrial materials has been a topic of considerable research using different approaches. Researchers have frequently used fabric samples to model the general problem of defect detection in various textured materials. Various approaches that use mean and standard deviation of sub blocks, gray level co-occurrence matrix, and autocorrelation of images have been used for characterization of fabric defects. At microscopic level, broad spectrum of different material inspection problems reduce to texture analysis problems. Several researchers have tried to address this problem with various approaches ranging from Gauss Markov Random Field (GMRF) modeling, Karhunen-Loève decomposition, Gabor filter, wavelet transform to neural networks.

Periodicity of yarns in textile webs results in Fourier domain features and has been used to explore fabric defects. U.S. Pat. No. 4,124,300 issued to Mead et al. on Nov. 7, 1978 discusses such an approach. Fourier transform based techniques are suitable for defects that cause global distortion of basic structure but unsuccessful for local defects that usually occur in small area of images. Consequently, detection of local fabric defects requires simultaneous measurements in spatial and spatial frequency domain. Accordingly, texture features based on Multiscale Wavelet Representation (MSWAR) has been used to detect local fabric defects. U.S. Pat. No. 5,815,198 issued to Vachtsevanos, et al. Sep. 29, 1998 discloses such an approach.

Ultrasonic transducers for inspecting industrial materials are also known. For example, U.S. Pat. No. 5,665,907 issued to Sheen et al. on Sep. 9, 1997 discloses an ultrasonic system for detecting fabric defects. U.S. Pat. No. 6,023,334 issued to Itagaki et al. on Feb. 8, 2000 discloses an approach of using brightness information to inspect homogenous surfaces such as plain aluminum sheets or plain glass.

The drawback of conventional approaches is that they are not sensitive enough to detect defect that produces subtle intensity transitions and consequently can not guarantee 100% inspection. Further, conventional approaches require statistical computations (e.g., mean and standard deviation) for their on-line implementation. Such computations are complex and require additional hardware.

Therefore, it is desirable to provide an inspection system that requires no on-line statistical computations. It is also desirable to provide a system which is capable of detecting defects that produce very subtle intensity transitions in acquired images. The present invention provides an inspection system that overcomes shortcomings of existing methods for defect detection.

SUMMARY OF THE INVENTION

The present invention relates to a method of inspecting a web material to detect defects. According to the present invention, the values of pixels in a defect-free region can be greatly attenuated relative to those in a defect region in various manners. For example, the energy of pixels in a defect-free region and in a defect region can be obtained to segment defects. In one embodiment, a finite impulse response filter (FIR) can be used to select those frequencies, which can discriminate the energy of a local defect-free region from that of a local defect region to thereby detect defects.

The present invention also relates to a filter device for inspecting a web material to detect defects. The filter device can be designed by first obtaining the correlation matrices from the fabric samples and the eigenvectors. Then, the eigenvector yielding the maximum object function can be selected. The optimal filter $h_{op}(x, y)$ can be obtained, such as by inversing lexicographical reordering.

BRIEF DESCRIPTION OF THE DRAWINGS

The present invention will become more apparent from the following description in conjunction with the accompanying drawings, in which:

FIGS. 3(a) through 3(i) show experimental results with a fabric sample having defect mispick, in which FIG. 3(a) shows a fabric sample with mispicks, FIG. 3(b) shows the image after filtering with a 7×7 optimal filter, FIG. 3(c) shows the local energy estimate of the image in FIG. 3(b), FIG. 3(d) shows segmented defects after thresholding the image of FIG. 3(b), FIG. 3(e) shows segmented defects after thresholding the image in FIG. 3(b), FIG. 3(f) shows two dimensional mesh plot of the local energy estimate, FIG. 3(g) shows two dimensional mesh plot of the thresholded image of FIG. 3(e), FIG. 3(h) shows the amplitude frequency response of the 7×7 optimal filter, and FIG. 3(i) shows the object function for each of the 49 eigenvectors.

FIGS. 4(a) through 4(p) show experimental results of fabric samples having defects detected with the optimal filters designed according to the present invention, in which FIGS. 4(a), 4(e), 4(i), and 4(m) show samples of a wrong-draw, a coloured yarn, a broken end, and a dirty yarn, respectively; FIGS. 4(b), 4(f), 4(j), and 4(n) show corresponding local energy estimates obtained by optimal filter designed with criterion function $J_1(h_{op})$; FIGS. 4(c), 4(g), 4(k), and 4(o) show corresponding local energy estimates obtained by optimal filter designed with criterion function $J_2(h_{op})$; and FIGS. 4(d), 4(h), 4(l), and 4(p) show corresponding local energy estimates obtained by optimal filter designed with criterion function $J_3(h_{op})$.

FIGS. 5(a) through 5(p) show detection results for fabric samples having defects, in which FIGS. 5(a), 5(e), 5(i), and 5(m) show samples of a double-weft, a big knot, a broken yarn, and a tripe-warp, respectively; FIGS. 5(b), 5(f), 5(j), and 5(n) show corresponding filtered images with optimal filters of the present invention; FIGS. 5(c), 5(g), 5(k), and 5(o) show corresponding local energy estimates; and FIGS. 5(d), 5(h), 5(l), and 5(p) show segmented defects.

FIGS. 6(a) through 6(d) show the detection results of defect mispick with 3×3 optimal filter mask, in which FIGS. 6(a) and 6(d) show the fabric samples; FIGS. 6(b) and 6(e) show local energy estimates; and FIGS. 6(c) and 6(d) show thresholded defects.

FIGS. 9(a) through 9(d) show the detection results for fabric defect in a vertical direction, in which FIG. 9(a) shows the fabric sample with mispick; FIG. 9(b) shows the image after filtering with an optimal filter; FIG. 9(c) shows local energy estimate of the image of FIG. 9(b); and FIG. 9(d) shows the segmented defect after thresholding the image of FIG. 9(b).

FIGS. 10(a) through 10(e) show the detection results for fabric defect detection with warp-weft model, in which FIG. 10(a) shows the fabric sample with a defect; FIG. 10(b) shows the output from optimal filter $h_1$; FIG. 10(c) shows the output from optimal filter $h_2$; FIG. 10(d) shows combined output from filters $h_1$ and $h_2$; and FIG. 10(e) shows segmented defect after thresholding the image of FIG. 10(d).

FIGS. 11(a) through 11(e) show the detection results for fabric defect detection with warp-weft model, in which FIG. 11(a) shows the fabric sample with a defect; FIG. 11(b) shows the output from optimal filter $h_1$; FIG. 11(c) shows the output from optimal filter $h_2$; FIG. 11(d) shows combined output from filters $h_1$ and $h_2$; and FIG. 11(e) shows segmented defect after thresholding the image of FIG. 11(d).

FIGS. 12(a) through 12(e) show the detection results for fabric defect detection with warp-weft model, in which FIG. 12(a) shows the fabric sample with a defect; FIG. 12(b) shows the output from optimal filter $h_1$; FIG. 12(c) shows the output from optimal filter $h_2$; FIG. 12(d) shows combined output from filters $h_1$ and $h_2$; and FIG. 12(e) shows segmented defect after thresholding the image of FIG. 12(d).

FIGS. 13(a) through 13(e) show the detection results for fabric defect detection with warp-weft model, in which FIG. 13(a) shows the fabric sample with a defect; FIG. 13(b) shows the output from optimal filter $h_1$; FIG. 13(c) shows the output from optimal filter $h_2$; FIG. 13(d) shows combined output from filters $h_1$ and $h_2$; and FIG. 13(e) shows segmented defect after thresholding the image of FIG. 13(d).

FIGS. 14(a) through 14(e) show the detection results for fabric defect detection with warp-weft model, in which FIG. 14(a) shows the fabric sample with a defect; FIG. 14(b) shows the output from optimal filter $h_1$; FIG. 14(c) shows the output from optimal filter $h_2$; FIG. 14(d) shows combined output from filters $h_1$ and $h_2$; and FIG. 14(e) shows segmented defect after thresholding the image of FIG. 14(d).

DETAILED DESCRIPTION OF THE INVENTION

Exemplary inspection method and apparatus embodying the principles of the present invention are shown throughout the drawings and will now be described in detail.

Figure 1:
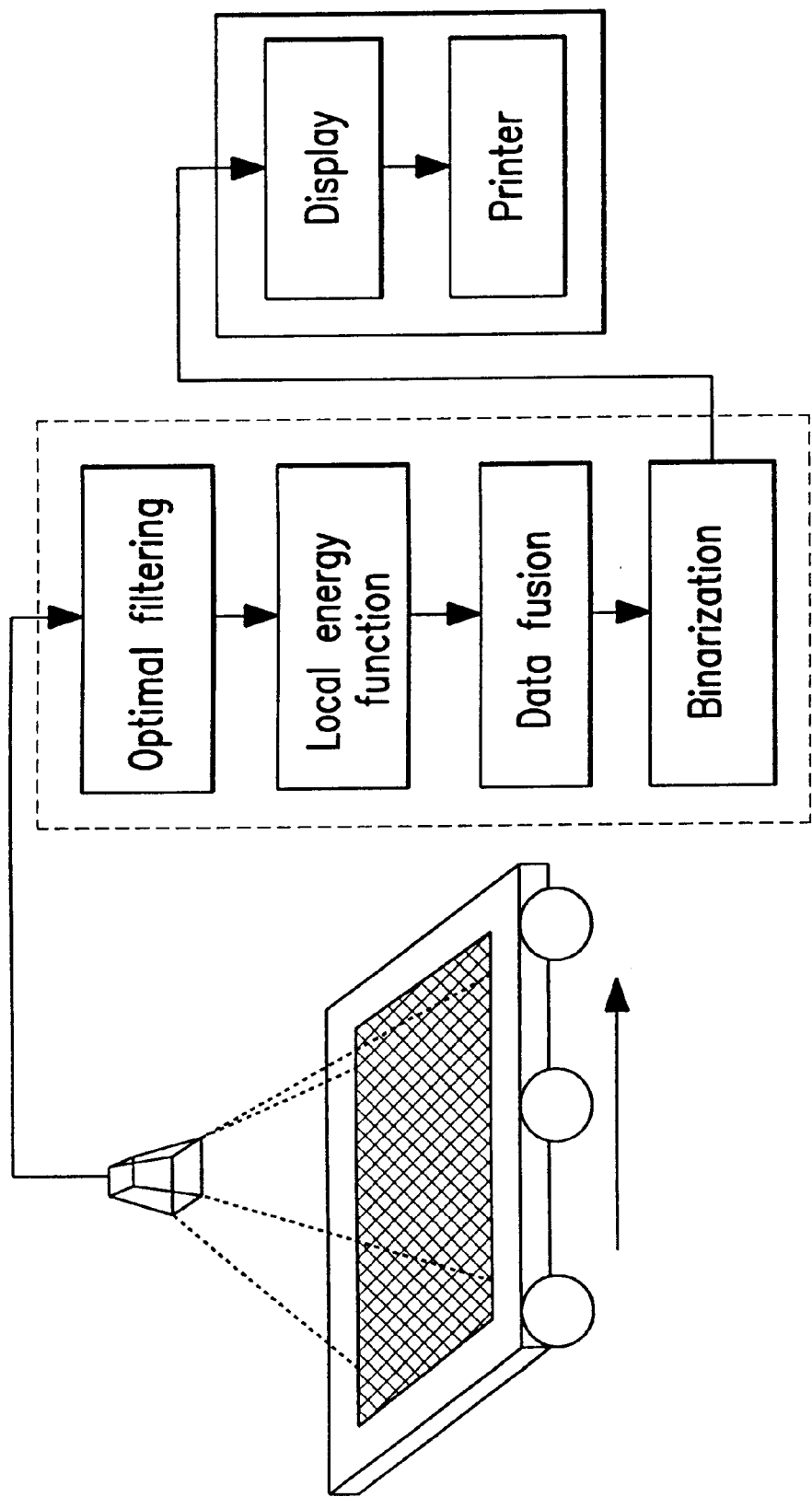
FIG. 1 is a block diagram of an inspection system incorporating an optimal filter formed according to the present invention.

FIG. 1 shows the block diagram of the present invention formed to inspect the image of and thereby detect defects on a web material. According to the present invention, the values of pixels in a defect-free region can be greatly attenuated relative to those in a defect region in various manners. For example, the energy of pixels in a defect-free region and in a defect region can be obtained to detect the defects. In a preferred embodiment, a finite impulse response (FIR) filter can be used to extract those frequencies from the inspection images which discriminate the energy of a local defect-free region from that of a local defect region. The details of optimal filters will be described below.

1. Mathematical Foundations

Figure 2:
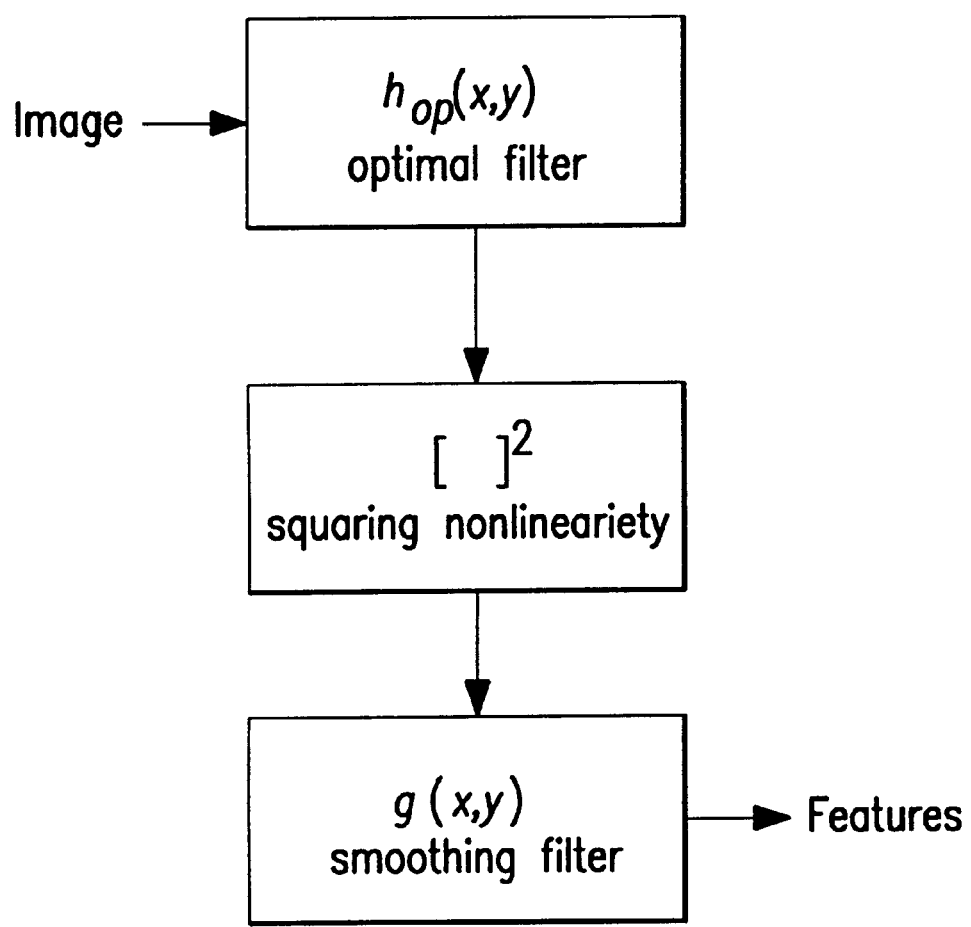
FIG. 2 shows a feature extraction model for forming the optimal filters of the present invention.

FIG. 2 shows an exemplary embodiment of a feature extraction model used to form an optimal filter of the present invention. In one embodiment, the texture in the image can be modeled by, such as an autocorrelation function of the texture. Energy can be extracted by, such as squaring non-linearity. The expression for the mean feature value and its derivative can be obtained by modeling the texture image. By selecting a suitable cost function for the optimization, the optimal filters can be designed by an iterative search or by generating a closed-form solution.

1.1. Local Energy Estimate

Each of the acquired images is assumed to be a random process and stationary in the region of interest. Let x and y be the spatial indices of an acquired image I(x, y). As shown in FIG. 2, filtering an acquired image I(x, y) with filter $h_{op}(x, y)$ can generate a new image w(x, y):

$$w(x, y) = h_{op}(x, y) * I(x, y) \tag{1}$$

$$= \sum_{m=0}^{M-1} \sum_{n=0}^{N-1} h_{op}(m, n) I(x-m, y-n),$$

wherein * denotes a two-dimensional convolution and $h_{op}(x, y)$ is an M×N optimal filter. For every pixel in w(x, y) the output can be rewritten as:

$$w(x, y) = h_{op}^T i(x, y), \tag{2}$$

wherein $h_{op}$ and i(x, y) are the vectors of length L=M×N obtained, such as by lexicographical ordering of columns of $h_{op}(x, y)$ and M×N window of I(x, y) around pixel (x, y) respectively.

$$i(x, y) = \begin{bmatrix} I(x, y) \\ \cdots \\ \cdots \\ I(x, y-N+1) \\ I(x-1, y) \\ \cdots \\ \cdots \\ I(x-M+1, y-N+1) \end{bmatrix} \tag{3}$$

$$h_{op} = \begin{bmatrix} h_{op}(0, 0) \\ \cdots \\ \cdots \\ h_{op}(0, N-1) \\ h_{op}(1, 0) \\ \cdots \\ \cdots \\ h_{op}(M-1, N-1) \end{bmatrix}$$

The energy at each pixel (x, y) can be obtained by passing w(x, y) through a squaring nonlinearity.

$$z(x, y) = w^2(x, y) \tag{4}$$

The energy of every pixel in z(x, y) is now calculated with reference to a local region around pixel at (x, y) to obtain a local energy estimate. The local region can be determined by the bandwidth of a smoothing filter. In one embodiment, the local energy estimate can be obtained by smoothing z(x, y) with a filter g(x, y), which will be further described in detail.

$$F(x, y) = z(x, y) * g(x, y) = w^2(x, y) * g(x, y) \tag{5}$$

As shown in the last block of FIG. 2, image features F(x, y) are the local energy estimates.

Assuming wide sense stationarity (WSS), the mean feature value $\mu_f$ and its derivative are modeled as follows:

$$\mu_{71} = E\{F(x, y)\}^* = E\{z(x, y) * g(x, y)\} = E\{w^2(x, y) * g(x, y)\}.$$

Assuming that smoothing filter coefficients are such that $\Sigma_{x, y} g(x, y) = 1$, we can further simplify the above equation as follows:

$$\mu_{71} = E\{w^2(x, y)\} = E\{(h_{op}^T i(x, y))(h_{op}^T i(x, y))\} = h_{op}^T E\{i(x, y) i^T(x, y)\} h_{op} = h_{op}^T R_{ii} h_{op} \tag{6}$$

wherein $R_{ii} = E\{i(x, y) i^T(x, y)\}$ is the correlation matrix and can be constructed from the autocorrelation function of the image i(x, y).

$$\frac{\partial \mu_f}{\partial h_{op}} = \frac{\partial h_{op}^T R_{ii} h_{op}}{\partial h_{op}} = 2 R_{ii} h_{op} \tag{7}$$

1.2. Object Functions for Optimization

The objective of designing optimal filters is to locate the defects contained in the acquired images. In the optimally filtered images, if the response to the defect is strong (e.g., bright), then the defect can be segmented by a linear two class discriminant classifier, typically thresholding. The average local energy estimate $\mu_{71_d}$ determines the brightness of F(x, y). We obtain the sample images of fabric with defect $I_d(x, y)$ and those without defect $I_r(x, y)$ as reference for feature extraction. Let $\mu_{f_d}$ and $\mu_{f_r}$ designate the average local energy estimates for fabric with defect and without defect, respectively. The object function $J_1(h_{op})$ evaluates the ratio of average local energy at the output of filter.

$$J_1(h_{op}) = \frac{\mu_{f_d}}{\mu_{f_d}} = \frac{h_{op}^T R_{ii_d} h_{op}}{h_{op}^T R_{ii_r} h_{op}} \tag{8}$$

Optimization of this object function $J_1(h_{op})$ can maximally separate the ratio of average feature values. For example, parameters of the optimal filter $h_{op}$ corresponding to maximum object function $J_1(h_{op})$ can be obtained by setting the gradient to zero.

$$\frac{\partial J_1(h_{op})}{\partial h_{op}} = \frac{2 R_{ii_d} h_{op}}{h_{op}^T R_{ii_r} h_{op}} - \frac{2 h_{op}^T R_{ii_d} h_{op} R_{ii_r} h_{op}}{[h_{op}^T R_{ii_r} h_{op}]^2} = 0$$

Setting $$\Psi = \frac{h_{op}^T R_{ii_d} h_{op}}{h_{op}^T R_{ii_r} h_{op}}$$

in the above equation yields, $$R_{ii_r}^{-1} R_{ii_d} h_{op} = \Psi \cdot h_{op} \tag{9}$$

This is an eigenvalue equation wherein the filter $h_{op}$ is the eigenvector and $\Psi$ is the eigenvalue. The expression for eigenvalue $\Psi$ is identical to $J_1(h_{op})$, the object function to be optimized. Therefore, the optimal filter is the eigenvector $h_{op}$ that yields maximum object function $J_1(h_{op})$.

Another object function, which has been used for optimal texture transform, can also be used for defect detection and is given below:

$$J_2(h_{op}) = \frac{(\mu_{f_d} - \mu_{f_r})^2}{\mu_{f_d} \mu_{f_r}}.$$

Closed-form optimization with respect to this object function $J_2(h_{op})$ can maximize the relative distance between the average value of local energy estimates.

$$\frac{\partial J_2(h_{op})}{\partial h_{op}} = \frac{\partial J_2(h_{op})}{\partial \mu_{f_d}} \frac{\partial \mu_{f_d}}{\partial h_{op}} + \frac{\partial J_2(h_{op})}{\partial \mu_{f_r}} \frac{\partial \mu_{f_r}}{\partial h_{op}} = 0 \tag{10}$$

Substituting equations (6) and (7) in equation (10) yields, $$R_{ii_r}^{-1} R_{ii_d} h_{op} = \Psi \cdot h_{op} \tag{11}$$

wherein $$\Psi = \frac{h_{op}^T R_{ii_d} h_{op}}{h_{op}^T R_{ii_r} h_{op}}. \tag{12}$$

Equation (11) is an eigenvalue equation. The optimal filter is given by eigenvector $h_{op}$ that yields maximum object function $J_2(h_{op})$. All eigenvectors $h_{op}$ satisfies equation (12), wherein $\Psi$ is the corresponding eigenvalue.

The optimal filters formed according to the above embodiments can achieve large separation of average local energy estimates $\mu_{f_d}$ and $\mu_{f_r}$. Additionally or alternatively, the optimal filter can be formed to take the variances of local energy estimates F(x, y) into account. The optimal filter so formed can at least minimize any possible overlap in feature distribution even if the variances of local energy estimate $\sigma_{f_d}$ and $\sigma_{f_r}$ are large. In an exemplary embodiment, the optimal filter can be formed so that it can not only produce large separation of mean local energy estimate but also yield low variances $\sigma_{f_d}$ and $\sigma_{f_r}$. For example, an object function that is commonly used in the pattern recognition literature is the Fisher criterion. The Fisher criterion takes the variances of the feature distributions into account.

$$J_3(h_{op}) = \frac{(\mu_{f_d} - \mu_{f_r})^2}{\sigma_{f_d}^2 + \sigma_{f_r}^2} \quad (13)$$

An approximate closed-form solution for computing optimal filters based on Fisher criterion function can be used in defect segmentation. By approximating fabric texture as autoregressive fields of order one, a simplified expression for variance and its derivative can be obtained. Optimization can be reduced to the following eigenvalue equation:

$$(R_{ii_r}^{-1} R_{ii_d}) h_{op} = \frac{(h_{op}^T R_{ii_d} h_{op})}{(h_{op}^T R_{ii_r} h_{op})} h_{op}. \quad (14)$$

The coefficients of the optimal filter can be computed from eigenvector $h_{op}$ that gives maximum value of the object function $J_3(h_{op})$.

According to the present invention, an optimal filter can be formed, such as by first obtaining the correlation matrices $R_{ii_r}$ and $R_{ii_d}$ from fabric samples and the eigenvectors of $(R_{ii_r}^{-1} R_{ii_d})$. Then, the eigenvector yielding the maximum object function, such as $J_1(h_{op})$ or $J_2(h_{op})$ or $J_3(h_{op})$, can be selected. The optimal filter $h_{op}(x, y)$ can be obtained from elements of $h_{op}$, such as by inversing lexicographical reordering. It will be appreciated that other feature extraction models for forming optimal filters are also within the scope of the present invention.

2. Supervised Defect Detection

In most industrial inspection systems, prior knowledge of defects to be detected is available. Inspection of such known defects can be regarded as supervised defect detection. The following embodiments describe such supervised defect detection using optimal filters designed to detect known categories of defects in web materials.

2.1. Size of Optimal Filter

The dimension of an FIR filter can be determined based on a variety of factors. For example, the dimension of an FIR filter can be determined based on its bandwidth. In general, filters with a large bandwidth have a smaller dimension than filters with a small bandwidth.

Additionally or alternative, the dimension of an optimal filter can be determined based on the spectral characteristics of a fabric image, such as yarn density and weaving pattern. For example, if the fabric material is a plain weave fabric with a high yarn density, then the image pixels of the fabric will become uncorrelated rapidly. Accordingly, the spectrum of such fabric can probably have a high frequency content which requires a large bandwidth or a spatial filter of a small dimension. In alternative, filters of a large spatial dimension can be used with a fabric material having a lower yarn density. Because a symmetric region of support is used for an accurate edge localization, therefore only odd sized filter masks are described below.

2.2. Selection of Smoothing Filter

An optimal filter of the present invention can comprise a smoothing filter. The smoothing filter is capable of transforming areas having a high local band pass energy to strong gray level distributions. In an exemplary embodiment, a Gaussian low pass smoothing filter is used. Such a Gaussian low pass smoothing filter is separable and capable of offering optimal joint resolution in spatial frequency and spatial domain.

$$g(x, y) = \frac{1}{\sqrt{2\pi}\lambda} e^{-((1/2)(x^2+y^2)/\lambda^2)} \quad (15)$$

The choice of bandwidth $\lambda$ can determine the frequencies to be included for local energy estimation at the output. Finite approximation of the filter of equation (15) above implemented as separable convolution masks can be used as a smoothing filter. In one embodiment, bandwidth $\lambda$ can be:

$$\lambda = \frac{1}{2\sqrt{2f_0}}. \quad (16)$$

The center frequency $f_o$ can be determined, such as by the number of pixels occupied by one yarn in an image. For example, in all twill fabric samples described in this application, one yarn occupies approximately 8 pixels. Accordingly, the center frequency $f_o = \frac{1}{8}$. When the image is filtered near the image boundary, we assume that the image is extended by its mirror image, i.e., even reflections.

2.3. Experimental Results

The present invention is applicable to various web materials, such as textile, paper, plastic, wood, and metal. In one embodiment, the samples used can be twill or plain fabric materials gathered from looms. Such sample materials can contain most common fabric defects, such as mixed filling, mispicks, kinky filling, misread, wrong-draw, coloured yarn, broken end, dirty end, double-weft, big not, broken yarn, triple-warp, and etc.

Images of the sample fabric materials can be obtained in various manners. In one embodiment, all images can be acquired under a backlighting condition. Additionally or alternatively, the images can cover an area of about 1.28× 1.28 inch$^2$ of the sample fabric material. The acquired images can then be digitized, such as in 256×256 pixels, with eight-bit resolution (i.e., 256 gray levels). These acquired images can be histogram equalized and then used for designing optimal filters as described below. In an exemplary embodiment, linear finite impulse response filters with optimized energy separation are used to segment defects. In a preferred embodiment, a Gaussian low pass filter as described above can be used for smoothing.

Figure 3A:
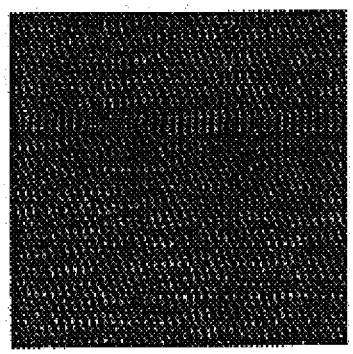

FIG. 3(a) shows the image of a sample twill fabric with a defect, such as a mispick. In one embodiment, a 7×7 optimal filter can be designed with the object function $J_1(h_{op})$ to segment the defect. FIG. 3(i) illustrates possible eigenvalues of equation (9). The eigenvector corresponding to the largest eigenvalue (4.4187) can be chosen to form the optimal filter. FIG. 3(h) shows magnitude frequency response of such an optimal filter. It can be seen that frequency response exhibits passbands where local energy estimate is high (corresponding to defect) and stopbands elsewhere.

Figure 3B:
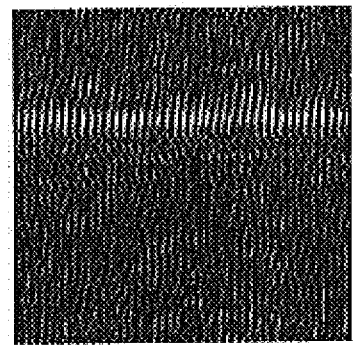

FIG. 3(b) shows the image after filtering with the optimal filter. As seen from the image, the standard deviation of individual pixels corresponding to defect is much higher than those in a defect free region. Therefore the defect can be segmented by any two class linear discriminant function, such as thresholding. The segmented defect and its three-dimensional mesh plot are shown in FIGS. 3(e) and 3(g), respectively.

Figure 3C:
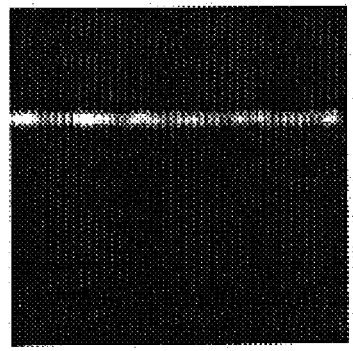
Figure 3D:
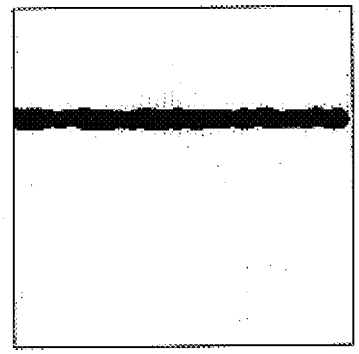
Figure 3E:
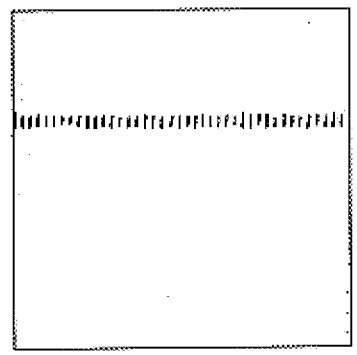
Figure 3F:
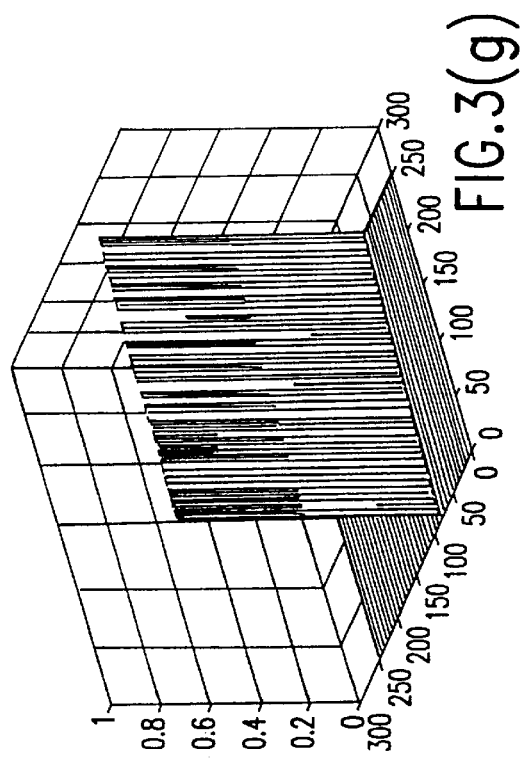
Figure 3G:
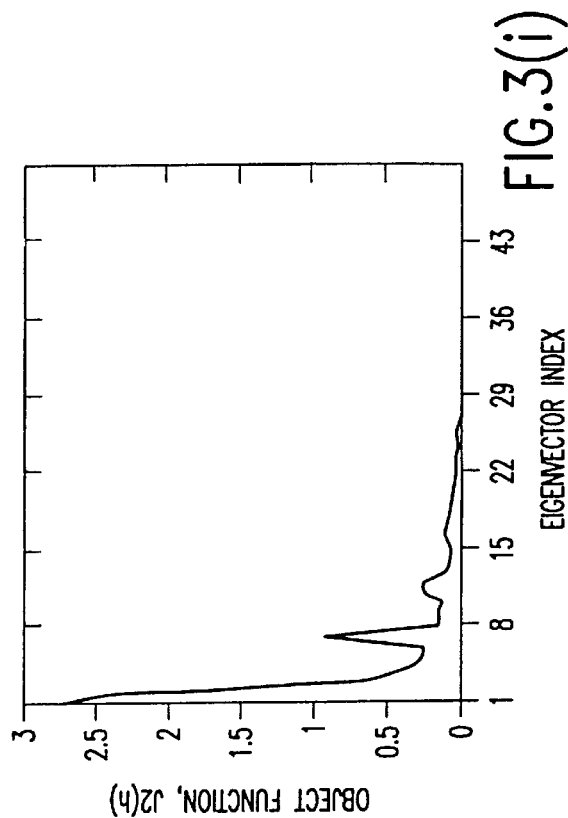
Figure 3H:
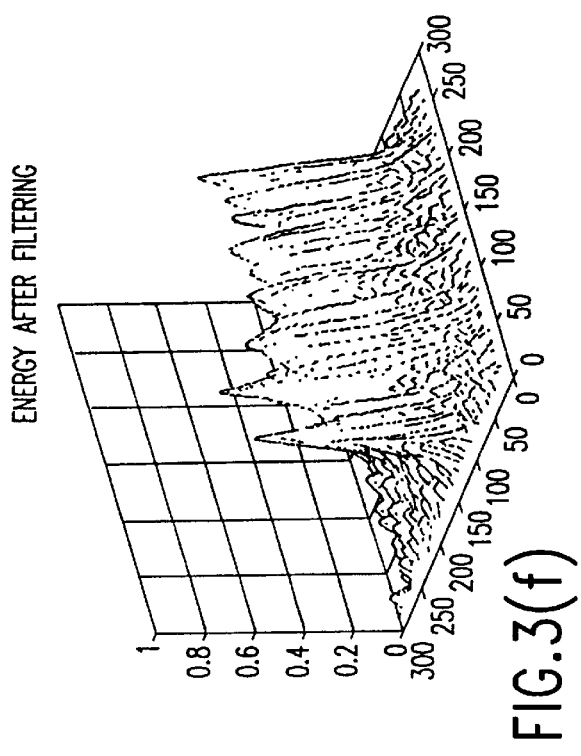
Figure 3I:
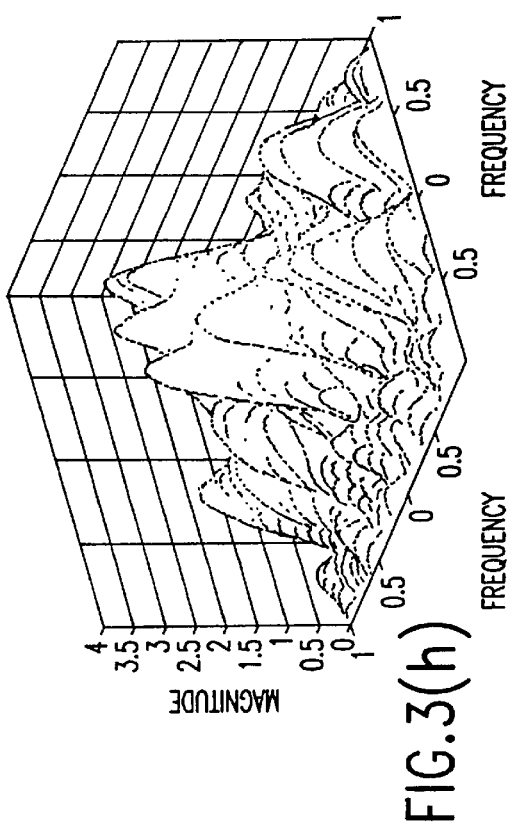

The local energy estimate for this sample image and its three-dimensional mesh plot are shown in FIGS. 3(c) and 3(f), respectively. Since the average local energy for the defect region is 4.4187 (from table 2) times than that of a defect-free region, the defect can be easily segmented, such as by a simple thresholding (FIG. 3(d)). The optimal filters are robust (as will be described below in section 3.3) and can successfully detect defects of similar nature located at any portion of the image under inspection. It will be appreciated that other embodiments of optimal filters are also within the scope of the present invention.

FIG. 4(a) shows the image of a plain weave fabric sample with a defect, such as a wrong-draw. In one embodiment, three 5×5 optimal filters having criterion functions $J_1(h_{op})$, $J_2(h_{op})$, and $J_3(h_{op})$ can be designed to detect the defect. The detection results of the three optimal filters are shown in FIGS. 4(b), 4(c), and 4(d), respectively, wherein all three optimal filters can successfully detect defects on the sample fabric.

Figure 4I:
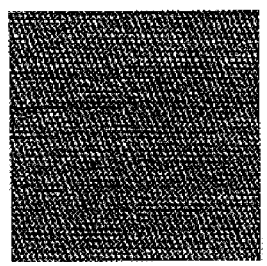
Figure 4J:
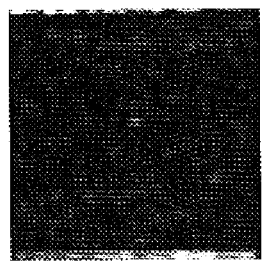
Figure 4K:
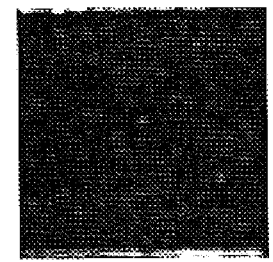
Figure 4L:
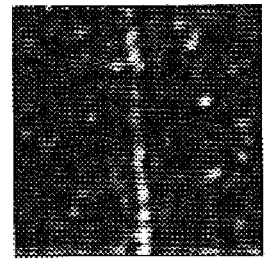
Figure 4M:
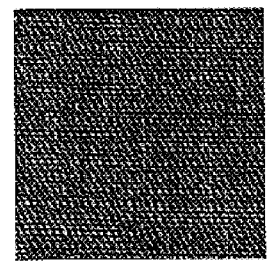
Figure 4N:
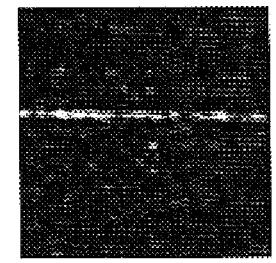
Figure 4O:
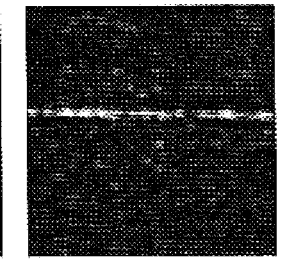
Figure 4P:
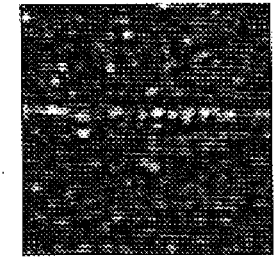

FIGS. 4(e) and 4(m) show twill weave fabric samples with defects, such as a coloured yarn and a dirty yarn, respectively. In one embodiment, these defects can be detected by using 7×7 optimal filters of the present invention. FIGS. 4(f) to 4(h) show the results for the fabric sample containing a coloured yarn inspected by optimal filters designed with $J_1(h_{op})$, $J_2(h_{op})$, and $J_3(h_{op})$, respectively. FIGS. 4(n) to 4(p) show the re for the fabric sample containing a dirty yarn inspected by optimal filters designed with $J_1(h_{op})$, $J_2(h_{op})$, and $J_3(h_{op})$, respectively.

In an alternative embodiment of FIG. 4(i), another twill weave fabric sample containing a defect, such as a broken end, is detected. FIGS. 4(j) and 4(k) show the detection results obtained by 7×7 optimal filters designed with $J_1(h_{op})$ and $J_2(h_{op})$, respectively. FIG. 4(l) shows the result of an optimal filter with the object function $J_3(h_{op})$ corresponding to the Fisher criterion. As described in the above embodiments, one or all three criterion functions $J_1(h_{op})$, $J_2(h_{op})$, and $J_3(h_{op})$ can be used to design optimal filters to detect a variety of defects in plain and/or twill weave fabrics. It will be appreciated that other embodiments of optimal filters are also within the scope of the present invention.

In one embodiment of the present invention, the optimal filter designed with the object function $J_2(h_{op})$ can yield preferred results that can be detected by a simple thresholding. Additional experimental results obtained by an optimal filter with object function $J_2(h_{op})$ are shown in FIGS. 5(a) through 5(p). FIGS. 5(a), 5(e), 5(i), and 5(m) show the images of fabric samples containing a double-weft, a big knot, a broken yarn, and a tripe-warp, respectively. FIGS. 5(b), 5(f), 5(j), and 5(n) show corresponding filtered images with the optimal filter with object function $J_2(h_{op})$. FIGS. 5(c), 5(g), 5(k), and 5(o) show corresponding local energy estimates. FIGS. 5(d), 5(h), 5(l), and 5(p) show segmented defects. The minimum mask size for each optimal filter used in the above embodiments and discussed in section 2.1 are shown in Table 1 below. The present invention can be applied to detect other fabric defects, such as slubs, loom fly, oil stain.

TABLE 1

Minimum Mask Size Required for Fabric Samples Used in Experiments

| Mask Size | 5 × 5 | 7 × 7 | 9 × 9 |
|---|---|---|---|
| Type of Fabric Sample | Plain | Twill | Plain |
| Yarn Density | High | Medium | Low |
| Wrap × Weft per inch | 136 × 72 | 118 × 60 | 110 × 52 |
| Figure Number(s) | 4(a), 5(a) | 4(e), 4(i), 4(m), 5(e), 5(i) | 5(m) |

2.4. Discussion

In general, high spatial resolution is required for an accurate preservation of edges. On the other hand, high spatial frequency resolution is required for an accurate estimation of local energy. Because spatial resolution and spatial frequency resolution are inversely related, both accurate edge localization and accurate local energy estimation are taken into consideration in determining the size of the smoothing filter.

The qualitative analysis is used for the detection results obtained in the present invention. Table 1 lists the minimum mask size used in each of the above experiments to detect the given category of defects with an "acceptable performance". Quantitatively an "acceptable performance" can denote that the percentage of misclassified defect pixels are less than about 10% in the final thresholded image. In one embodiment of the present invention, the noise shown in the detection results of FIG. 5 can be reduced to zero when the mask size is increased, such as to those shown in Table 1. In another embodiment, optimal filters with a smaller size can be used to detect fabric samples with a higher yarn density and vice versa. The size of optimal filter masks required to detect a defect can depend on other factors, such as the spectral characteristics of a defect and the accuracy required for the detection.

Table 2 shows the magnitude of the three object functions as a function of mask size. The second column in this table shows the average energy of pixels in the defect region relative to that of defect-free region in the filtered image. When the mask size increases from 3×3 to 5×5 (7×7), computation time for filtering with $J_1(h_{op})$ increases by 77 (340) %, but the object function only increases by 1 (114) %. This defect can also be detected by a 3×3 mask (FIG. 3(a)) with marginal compromise on performance.

TABLE 2

Maximum Object Function (for mispick as shown in FIG. 3(a)) as a Function of Mask Size

| Mask Size | $J_1(h_{op})$ | $J_2(h_{op})$ | $J_3(h_{op})$ |
|---|---|---|---|
| 3 × 3 | 1.4082 | 0.1183 | 0.4063 |
| 5 × 5 | 2.8315 | 1.1846 | 1.0283 |
| 7 × 7 | 4.4187 | 2.6450 | 0.9406 |
| 9 × 9 | 5.5855 | 3.7645 | 1.0117 |
| 11 × 11 | 6.6410 | 4.7916 | 1.0602 |
| 13 × 13 | 7.8826 | 6.0094 | 0.9269 |
| 15 × 15 | 8.8267 | 6.9399 | 1.1859 |
| 17 × 17 | 9.8922 | 7.9932 | 1.6401 |
| 19 × 19 | 10.8588 | 8.9509 | 1.3436 |

FIG. 6 shows that this 3×3 mask can detect other mispicks in the same direction. In another embodiment, the minimum mask size used for defect detection can depend on the nature (spectrum) of the defects. For example, the choice of the weakest eigenvector corresponding to the smallest eigenvalue (i.e., object function) can generate an inverse solution, i.e., gray levels in a filtered image are interchanged from the maximum to the minimum.

In another embodiment, fabric samples that require careful manual (visual) inspection for defect detection are tested with 7×7 optimal filters. It is preferred that an optimal filter based on object function $J_3(h_{op})$ is used for detecting such defects because the Fisher criterion function also takes variances of the extracted features into account and is expected to perform better in many cases.

3. On-line Defect Detection

Industrial web inspection in production lines requires continuous processing of images acquired from camera using backlighting. Any online inspection system must be capable of integrating faults appearing at different orientations and resolution levels. The desired procedure must be robust, automatic, and flexible for a range of products to be inspected. The present invention also relates to an unsupervised defect detection for inspect web materials containing a large variety of defects.

Figure 7:
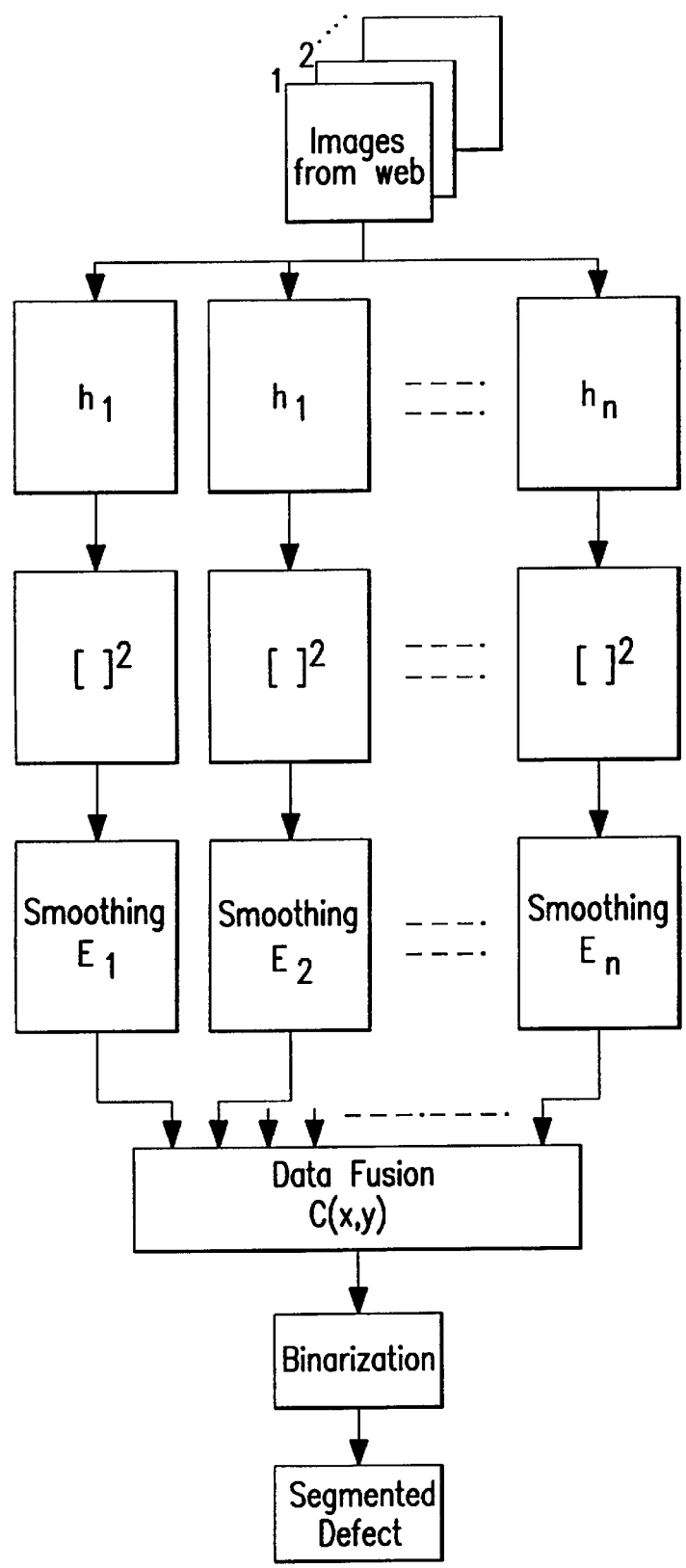
FIG. 7 is a block diagram of optimal filter based web inspection according to the present invention.

FIG. 7 shows a web inspection system according to the present invention, which comprises optimal filters designed according to the present invention. The algorithm proposed here is similar to other pattern recognition paradigms in that the process is divided into training and testing phases. The training process is offline and involves computations of optimal filters from sample images with defects. The testing phase is an online process, in which acquired images are inspected for defects using the pre-computed optimal filters.

As shown in FIG. 7, $h_1 \ldots h_n$ represent a set of n minimal optimal filters needed to capture the different types of defects for an acceptable performance. The total number of filters can be determined based on various factors, such as the range of defects to be detected (quality assurance) and the available computational complexity of hardware. For each optimal filtered output, a local energy estimate ($E_1 \ldots E_n$) is obtained, such as using the process described in section 1.1.

3.1. Data Fusion

A data fusion module is used in the present invention to integrate useful information from different channels, i.e., $E_1 \ldots E_n$. The image fusion module is capable of attenuating background pixels and accentuating pixels from the defect. In one embodiment, data fusion module can involve vector addition of component images. In alternative, Bernoulli's rule of combination can be used to combine images from different channels. In another embodiment, image fusion for reducing false alarm can be carried out by obtaining distance images $d_j(x, y)$ before their vector addition.

$$d_j(x, y) \Big|_{j=1 \ldots n} = \begin{cases} E_j(x, y) & |E_j(x, y) - v_j| \geq |\zeta \rho_j| \\ 0 & \text{Otherwise} \end{cases} \quad (17)$$

In the above equation, $v_j$ and $\rho_j$ are obtained from a defect free sample. In an embodiment, the local energy estimates from the optimal filters for the defect free samples can be obtained before online inspection. Mean $v_j$ and standard deviations $\rho_j$ from each of these images are used to generate distance images $d_j(x, y)$ (equation 17), vector addition of which can generate a fused image output. The variable $\zeta$ controls the sensitivity. In one embodiment, variable $\zeta$ can be fixed in the range between one to three.

3.2. Binarization

The next stage is the thresholding of the fused image output to generate a binary image of defects $B(x, y)$. A threshold value can be selected so that any value below this limit is considered to belong to a regular texture under inspection and any value above the limit is contributed from defects. The threshold value can be determined in various ways. In one embodiment, the threshold value can be obtained by calibration at the beginning of the operation. For example, a defect free sample is used to generate a fused image output $C_r(x, y)$. The threshold value $\Phi_{th}$ can be obtained as follows:

$$\Phi_{th} = \max \{C_r(x, y)\}_{x,y \in W} \quad (18)$$

wherein 'W' is a window centered at the image $C_r(x, y)$. The window size can be determined to avoid effects from border distortions. In an exemplary embodiment, the window size can be 20 pixels removed from each side of the image $C_r(x, y)$. It will be appreciated that other embodiments for obtaining threshold value are also within the scope of the present invention.

3.3. Warp-Weft Filter Model

Figure 8:
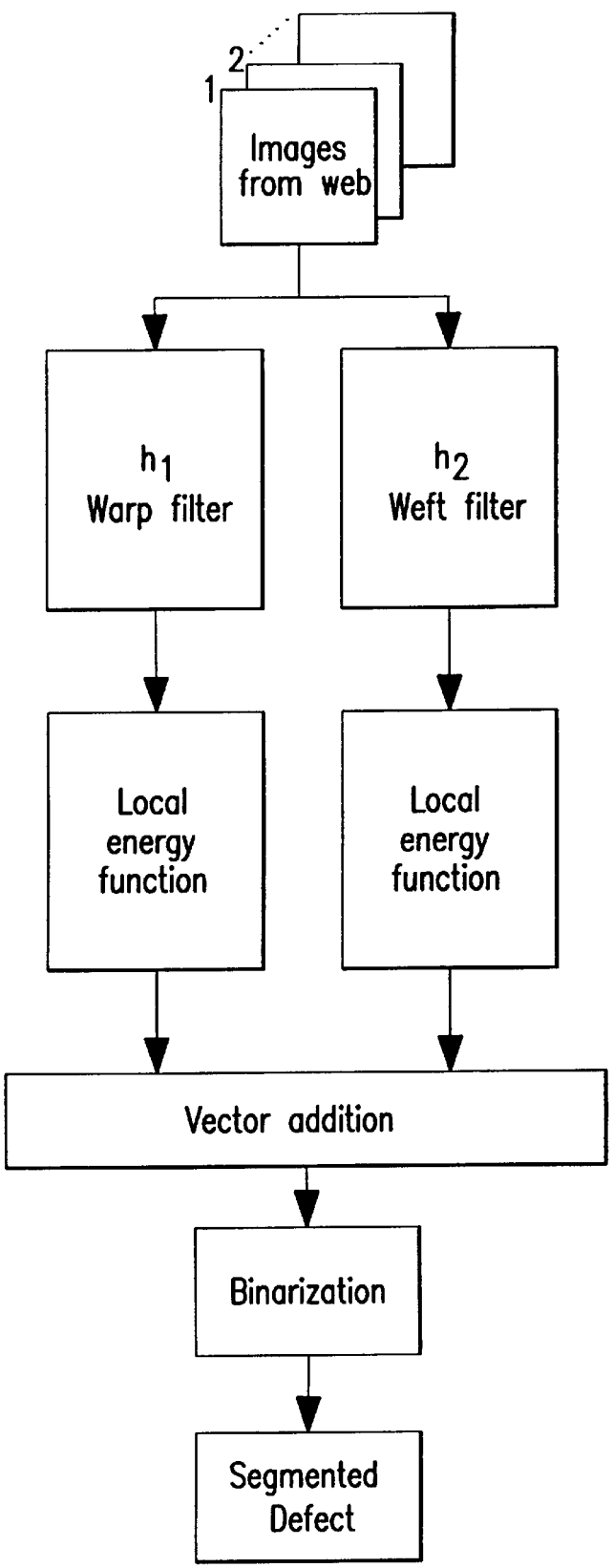
FIG. 8 is a block diagram of warp-weft model used for inspecting a web material according to the present invention.
Figure 9A:
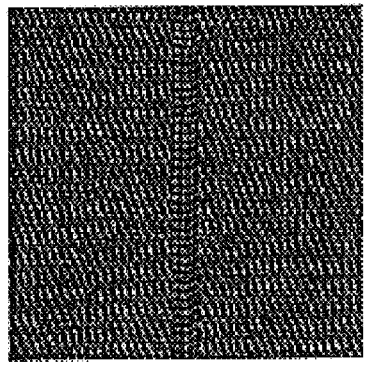
Figure 9B:
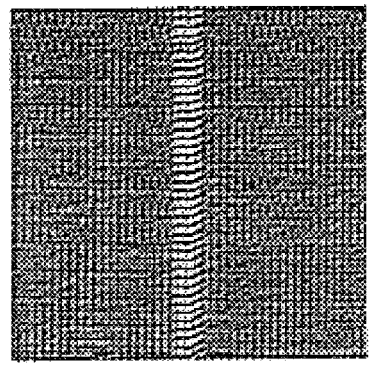
Figure 9C:
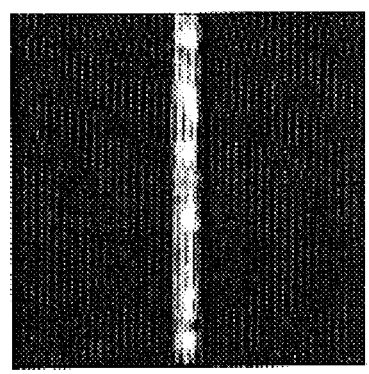
Figure 9D:
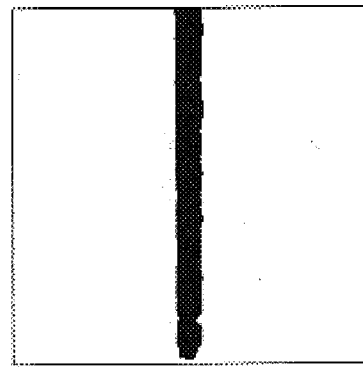

In an exemplary embodiment, the online defect detection algorithm can be evaluated using fabric samples gathered from textile looms. Defects on textile webs are usually located in either horizontal or vertical direction due to the nature of the weaving process in textile looms. Therefore, a warp-weft model using two optimal filters can be developed to detect defects in the horizontal (weft) direction and the vertical (warp) direction, as shown in FIG. 8. In one embodiment, the optimal filters are designed with an object function $J_2(h_{op})$. A 7×7 optimal filter mask $h_1$ can be designed to detect the fabric defect as shown in FIG. 9(a). The local energy estimate of the filtered image is shown in FIG. 9(c).

In an alternative embodiment, another fabric sample with a defect in the vertical direction (e.g., FIG. 3(a)) can be chosen. A 7×7 optimal filter $h_2$ can be designed similarly to that in section 2.3 to segment the defect. The data fusion module using a simple vector addition of local energy estimates ($E_1 \ldots E_n$) can be adequate with the resolution of the images used. The threshold limit $\Phi_{th}$ can be obtained as described in equation (17).

3.4. Experimental Setup and Results

The present invention is applicable for inspecting web materials containing most common fabric defects, such as mixed filling, mispicks, kinky filling, misread, wrong-draw, coloured yarn, broken end, dirty end, double-weft, big not, broken yarn, triple-warp, and etc. Accordingly, the warp-weft model of the present invention is proved to be robust. The following embodiments illustrate the detection results for twill weave fabric samples.

Figure 10A:
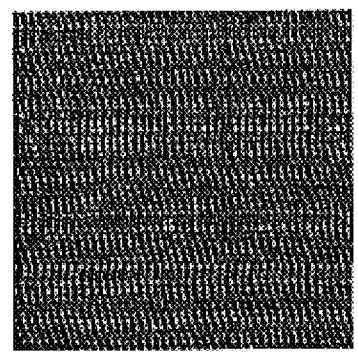
Figure 10B:
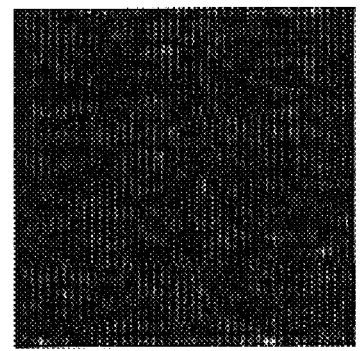
Figure 10C:
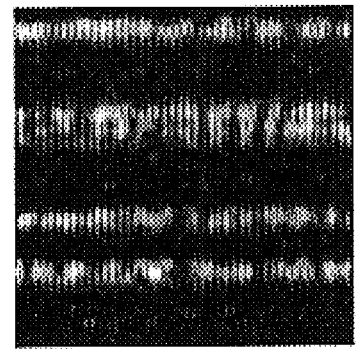
Figure 10D:
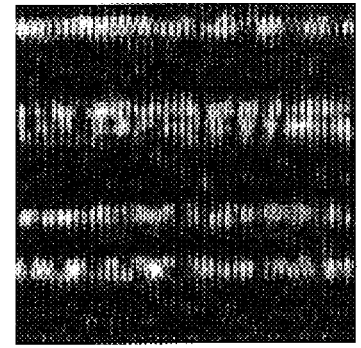
Figure 10E:
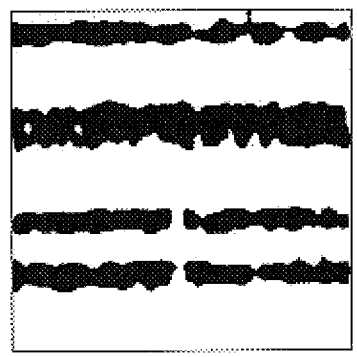
Figure 11A:
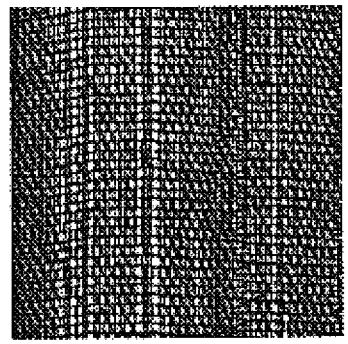
Figure 11B:
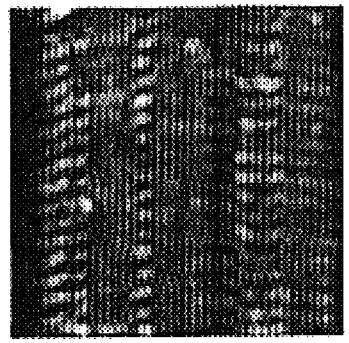
Figure 11C:
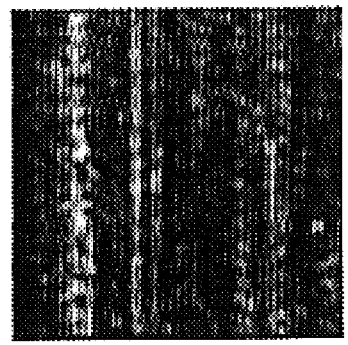
Figure 11D:
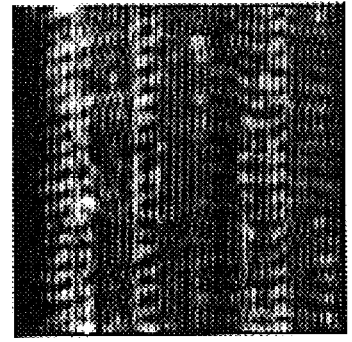
Figure 11E:
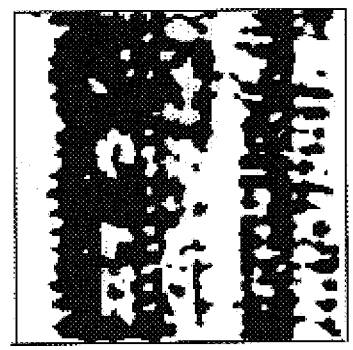
Figure 12A:
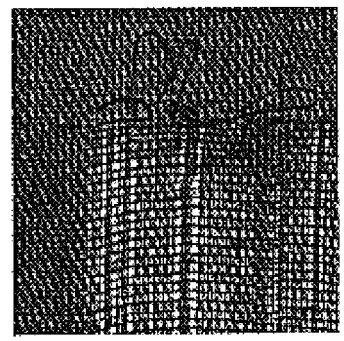
Figure 12B:
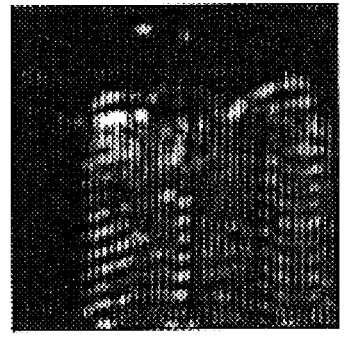
Figure 12C:
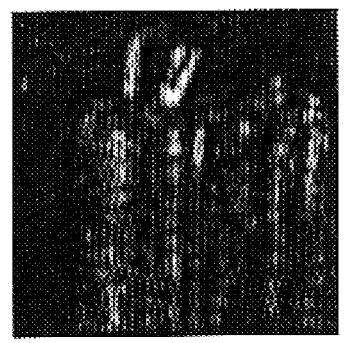
Figure 12D:
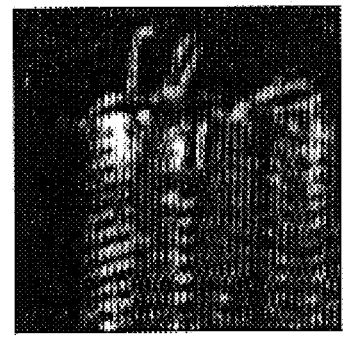
Figure 12E:
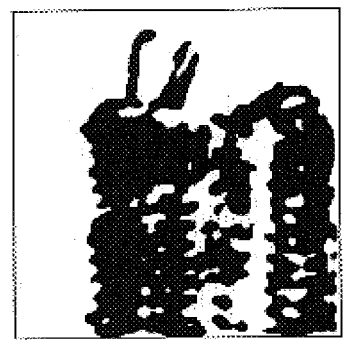
Figure 13A:
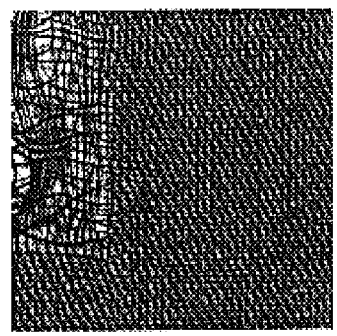
Figure 13B:
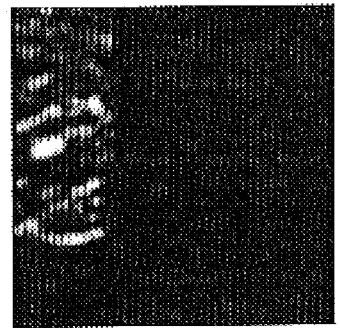
Figure 13C:
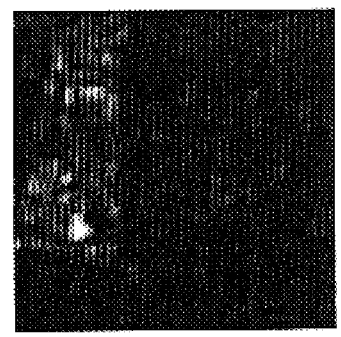
Figure 13D:
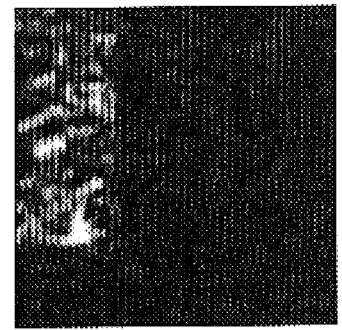
Figure 13E:
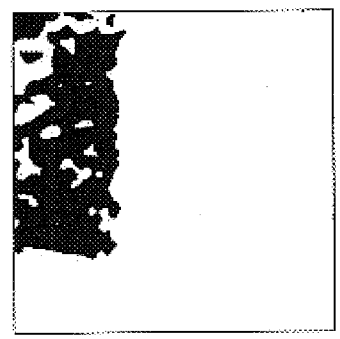

FIG. 10(a) shows a fabric sample containing defects, such as mispicks, in a vertical direction. In one embodiment, a filter $h_2$ can be used to contribute to the output shown in FIGS. 10(c) and 10(d). In another embodiment, a fabric sample contains defects shown in FIG. 11(a). In this embodiment, two filters $h_1$ and $h_2$ can be used, the results of which are shown in FIGS. 11(b) and 11(c), respectively. In the embodiment shown in FIGS. 12(b) and 12(c), filters $h_1$ and $h_2$ successfully capture the components of defects in the two directions. Similarly, FIGS. 13(b) and 13(c) depict components of fabric defects in FIG. 13(a). FIG. 14 shows another example of robustness of two filters to capture defects in two directions. The components in this defect slack-end are evenly distributed in horizontal and vertical directions. The respective components are captured and shown in FIGS. 14(b) and 14(c), respectively. FIG. 14(e) shows the segmented defect.

The present invention provides a new web inspection system based on optimal filters. On the basis of high performance coupled with low computational requirements, optimal filters can yield low cost solution to industrial inspection problems. The commercial applications of the present invention can ensure the quality assurance, which in turn will increase the efficiency of production lines. The optimal filters of the present invention can also be used to improve existing inspection systems based on other techniques that fail to detect a class of specific defects. Many of the existing inspection systems based on prior art offers very low detection rate for defects that produce very subtle intensity transitions. In such cases, the present invention based on optimal filters can be supplemented to detect these defects.

It will be appreciated that the various features described herein may be used singly or in any combination thereof.

Thus, the present invention is not limited to only the embodiments specifically described herein. While the foregoing description and drawings represent a preferred embodiment of the present invention, it will be understood that various additions, modifications, and substitutions may be made therein without departing from the spirit and scope of the present invention as defined in the accompanying claims. In particular, it will be clear to those skilled in the art that the present invention may be embodied in other specific forms, structures, and arrangements, and with other elements, and components, without departing from the spirit or essential characteristics thereof. One skilled in the art will appreciate that the invention may be used with many modifications of structure, arrangement, and components and otherwise, used in the practice of the invention, which are particularly adapted to specific environments and operative requirements without departing from the principles of the present invention. The presently disclosed embodiment is therefore to be considered in all respects as illustrative and not restrictive, the scope of the invention being indicated by the appended claims, and not limited to the foregoing description.

What is claimed is:

1. A method of inspecting a web material containing defects, the method comprising:

acquiring an image of the web material, the acquired image comprising a plurality of pixels;

attenuating the pixels in the acquired image corresponding to a defect free region;

obtaining the energy of each pixel; and segmenting the defects.

2. The method of claim 1, wherein the acquired image is filtered.

3. The method of claim 1, wherein an optimal filter is used to attenuate the pixels in the acquired image corresponding to a defect free region.

4. The method of claim 1, wherein a nonlinear function is used to obtain the energy of each pixel.

5. The method according to claim 4, wherein the nonlinear function is squaring and absolute values of each filtered pixel.

6. The method of claim 1 further comprising obtaining a local energy estimation for each pixel in a local region.

7. The method of claim 6, wherein a smoothing filter is used to compute the local energy estimation of each pixel in a local region around the pixel.

8. The method of claim 1, wherein the acquired images are thresholded to segment the defects.

9. The method of claim 1, wherein the web material under inspection is selected from the group consisting of paper, fabric, plastic wood, and steel.

10. A method of inspecting unsupervised web materials containing defects, the method comprising:

designing a plurality of optimal filters for different categories of defects;

combining the output from each of the optimal filters in a data fusion module to obtain a fused output image; and segmenting defects in the fused output image.

11. The method of claim 10, wherein defects in the fused output image are segmented by thresholding.

12. The method of claim 10, wherein the web material comprises a woven material.

13. The method of claim 10, wherein two filters for horizontal and vertical directions are used.

14. The method of claim 10, wherein the web material under inspection is selected from the group consisting of paper, fabric, plastic, wood, and steel.

15. A method of inspecting defects in textured materials for industrial automation, the method comprising:

imaging the material under inspection;

using pre-designed optimal filters to attenuate pixels in acquired images corresponding to a defect free region;

using a nonlinear function to compute energy of each pixel;

using a smoothing filter to compute energy of every pixel in a local region; and thresholding the acquired images to segment the defects.

16. The method of claim 15, wherein the pre-designed optimal filters include at least one filter device for detecting a fabric defects, the filter comprising an optimal object function of:

$$J_1(h_{op}) = \frac{\mu_{f_d}}{\mu_{f_r}} = \frac{h_{op}^T R_{ii_d} h_{op}}{h_{op}^T R_{ii_r} h_{op}}$$

wherein $\mu_{f_d}$ and $\mu_{f_r}$ designate the average local energy estimate for a fabric with defect and without defect, respectively; and wherein $Rii = E\{i(x,y)i^r(x,y)\}$ is the L×L(L=M× N) correlation matrix and can be constructed from the autocorrelation function of the image i(x,y).

17. The method of claim 15, wherein the pre-designed optimal filters include at least one filter device for detecting fabric defects, the filter being designed to optimize the object function of:

$$J_2(h_{op}) = \frac{(\mu_{f_d} - \mu_{f_r})^2}{\mu_{f_d} \mu_{f_r}}$$

wherein $\mu_{f_d}$ and $\mu_{f_r}$ designate the average local energy estimate for a fabric with defect and without defect, respectively.

18. The method of claim 15, wherein the pre-designed optimal filters include at least one filter device for detecting fabric defects, the filter being designed to optimize the object function of:

$$J_3(h_{op}) = \frac{(\mu_{f_d} - \mu_{f_r})^2}{\sigma_{f_d}^2 + \sigma_{f_r}^2}$$

wherein $\mu_{f_d}$ and $\mu_{f_r}$ designate the average local energy estimate for a fabric with defect and without defect, respectively; and $\sigma_{f_d}$ and $\sigma_{f_r}$ designate variances of local energy estimate.

* * * * *